(12) United States Patent
Zhu et al.

(10) Patent No.: US 9,049,979 B2
(45) Date of Patent: Jun. 9, 2015

(54) USER INTERFACE SYSTEM AND METHOD FOR CREATING AND MANAGING ULTRASOUND MEASUREMENT-BASED CALCULATIONS IN ULTRASOUND IMAGING SYSTEM

(75) Inventors: Iris Zhu, Seattle, WA (US); Dan Skyba, Snohomish, WA (US); Cedric Chenal, Kirkland, WA (US)

(73) Assignee: Koninklijke Philips N.V., Eindhoven (NL)

( * ) Notice: Subject to any disclaimer, the term of this patent is extended or adjusted under 35 U.S.C. 154(b) by 2011 days.

(21) Appl. No.: 12/088,097

(22) PCT Filed: Sep. 26, 2006

(86) PCT No.: PCT/IB2006/053502
§ 371 (c)(1),
(2), (4) Date: Mar. 26, 2008

(87) PCT Pub. No.: WO2007/036879
PCT Pub. Date: Apr. 5, 2007

(65) Prior Publication Data
US 2008/0255448 A1    Oct. 16, 2008

Related U.S. Application Data

(60) Provisional application No. 60/722,292, filed on Sep. 30, 2005.

(51) Int. Cl.
*A61B 8/00* (2006.01)

(52) U.S. Cl.
CPC . *A61B 8/00* (2013.01); *A61B 8/465* (2013.01); *A61B 8/467* (2013.01)

(58) Field of Classification Search
CPC .......... A61B 8/00; A61B 8/465; A61B 8/467
USPC ........................................................ 705/2
See application file for complete search history.

(56) References Cited

U.S. PATENT DOCUMENTS

| | | | | |
|---|---|---|---|---|
| 5,553,620 | A * | 9/1996 | Snider et al. | 600/440 |
| 5,950,002 | A | 9/1999 | Hoford et al. | |
| 6,458,081 | B1 | 10/2002 | Matsui et al. | |
| 2004/0207661 | A1 * | 10/2004 | Akaki | 345/764 |
| 2005/0049493 | A1 | 3/2005 | Kerby et al. | |

FOREIGN PATENT DOCUMENTS

| | | |
|---|---|---|
| EP | 1454585 A | 9/2004 |
| WO | 01/23905 A | 4/2001 |

* cited by examiner

*Primary Examiner* — Hiep V Nguyen (57) ABSTRACT

An ultrasound imaging system (10) includes a display (16) for displaying an ultrasound image and an analysis package operatively connected to the image display. The analysis package provides a user the ability to manage an ultrasound measurement-based calculation. The analysis package facilitates the management of the measurement-based calculation by displaying for the user a sequence of data entry steps. Information necessary for managing the calculation is accepted and verified at each step and then, also used to determine which step to display next. At the conclusion of the final step, the measurement-based calculation is saved in the system.

5 Claims, 7 Drawing Sheets

USER INTERFACE SYSTEM AND METHOD FOR CREATING AND MANAGING ULTRASOUND MEASUREMENT-BASED CALCULATIONS IN ULTRASOUND IMAGING SYSTEM

This invention relates to medical ultrasound imaging systems and, more particularly, to a user interface in an ultrasound imaging system that allows for creation and management of measurement-based calculations.

Ultrasonic imaging systems routinely include visual tools by which a sonographer can measure anatomy shown in ultrasound images and calculate values and estimations from these measurements. Such measurements and calculations are quantified measures by reason of the spatially accurate dimensions and scaling with which ultrasound images can be displayed.

A typical use of such measurement and analysis tools can be found in ultrasound systems configured for obstetrical examinations. Obstetrical images can show anatomy such as the head, abdomen and limbs of the developing fetus. These anatomical features can be measured by placing markers and shapes over and around the features with the measurement tools. Measurements such as lengths and areas can be determined from the markers and shapes placed or drawn on the image. Some of the measurements can be directly diagnostic such as determining from the head circumference whether a Caesarian section delivery will be necessary. The measurements can also be used to compute other attributes of the developing fetus, such as estimated gestational age and fetal weight. The ability to make these measurements and calculations thus facilitates proper care and treatment of both the mother and baby.

More sophisticated ultrasound systems, particularly those that can be configured for a variety of clinical applications, are often equipped with the ability to perform dozens of measurements and calculations. As is well known in the art, such a system typically has greater flexibility and versatility than simply designating a default list of measurements and calculations. Such prior art systems typically allow the sonographer to design custom protocols which include custom measurements and calculations not provided by the manufacturer on the ultrasound system. This valuable feature frees the sonographer from the restricted use of only the measurements and calculations provided with the ultrasound system and variations thereof, and enables researchers to develop their own new and more accurate measures and computations which are better adapted to the demographics of their patient population.

Due to user interface limitations in prior art systems, however, development and implementation of custom protocols, measurements and calculations is cumbersome and not intuitive. In such prior art systems, the user interface presented to the sonographer for creating custom calculations is typically monolithic and features a single screen with many data fields. Any particular field may or may not be required for completing a particular operation. Which fields are, in fact, required is not immediately obvious. Such an interface is not intuitive and imposes on the sonographer the burden of learning how to use the interface to create or edit a custom calculation.

There is therefore a need for a system that provides the sonographer with a more streamlined and intuitive method and interface for creating custom calculations.

The present invention is directed to a medical ultrasound system and method for creating and managing custom measurement-based calculations. A sonographer may use such equipment to create images of internal organs and blood vessels, which are displayed on a screen. The ultrasound equipment provides the sonographer with the ability to make onscreen measurements of components of these images. These measurements are then used to derive various calculations useful for clinical and diagnostic purposes. Medical ultrasound equipment typically provides numerous such calculations by default. The ultrasound imaging system and method provides a user interface for creating and managing new custom measurements and calculations beyond those that are provided by the manufacturer. The system and method provides a sequential display of the operations required for any particular management function being carried out on the custom calculation. The system and method may further require the sonographer to input information, which is verified for consistency and correct syntax prior to the next input operation. Additionally, the system and method uses the information gathered in any particular operation to determine which operation the sonographer is presented with next. Lastly, the system and method allows the sonographer to save the custom calculation in the system for later recall. Simplifying management tasks in this manner, into discrete functional steps, increases sonographer efficiency by providing a streamlined and intuitive method and interface for creating custom calculations. Each input screen can be designed with an adequate amount of help and guidance so that the user does not have to constantly refer to system manuals for these operations.

Figure 1:
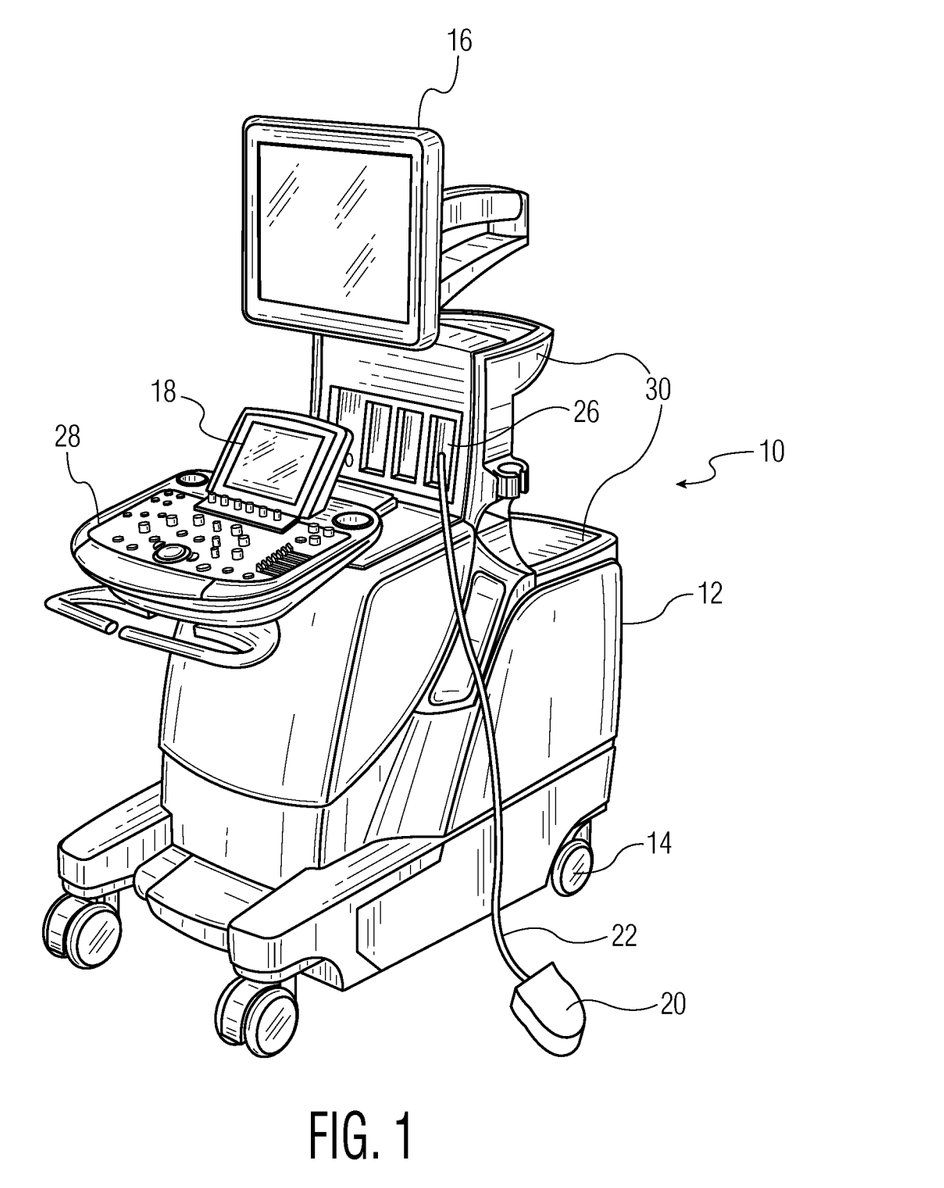
FIG. 1 is an isometric view of an ultrasound imaging system according to one example of the invention.

An ultrasound imaging system 10 according to one example of the invention is illustrated FIG. 1. The system 10 includes a chassis 12 containing most of the electronic circuitry for the system 10. The chassis 12 is mounted on a cart 14, and a display 16 is mounted on the chassis 12. An imaging probe 20 is connected through a cable 22 to one of three connectors 26 on the chassis 12. The chassis 12 includes a keyboard and controls, generally indicated by reference numeral 28, for allowing a sonographer to operate the ultrasound system 10 and enter information about the patient or the type of examination that is being conducted. At the back of the control panel 28 is a touchscreen display 18 on which programmable softkeys are displayed for supplementing the keyboard and controls 28 in controlling the operation of the system 10.

In operation, the imaging probe 20 is placed against the skin of a patient (no t shown) and held stationary to acquire an image of blood or tissues in a volumetric region beneath the skin. The image is presented on the display 16, and it may be recorded by a recorder (not shown) placed on one of the two accessory shelves 30. The system 10 may also record or print a report containing text and images. Data corresponding to the image may also be downloaded through a suitable data link, such as the Internet or a local area network. In addition to using the probe 20 to produce an image on the display, the ultrasound imaging system may also provide other types of information such as graphs and reports, and it may accept other types of probes (not shown) to provide other types of images.

Figure 2:
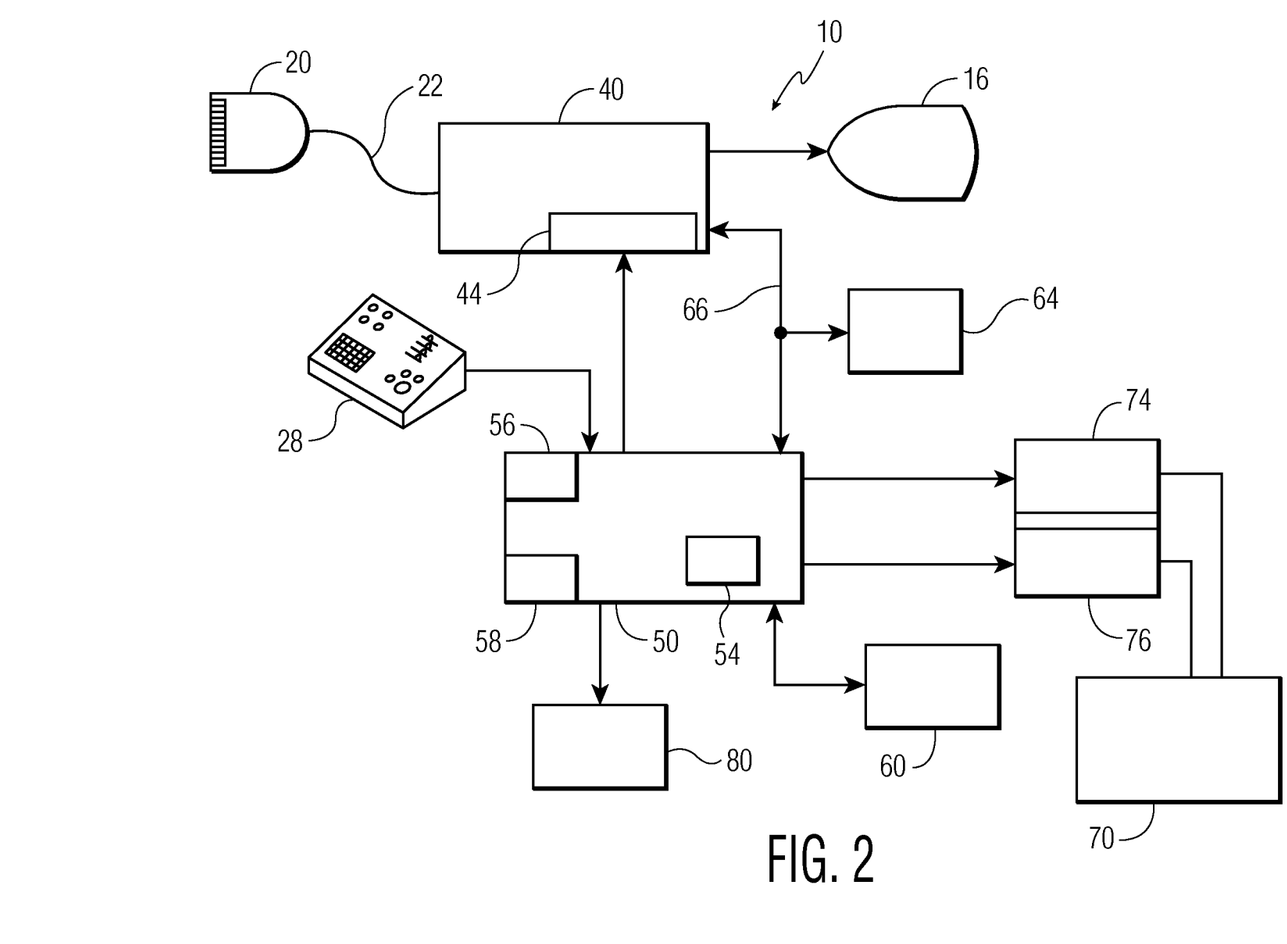
FIG. 2 is a block diagram of the electrical components used in the ultrasound imaging system of FIG. 1.

The electrical components of the ultrasound imaging system 10 are illustrated in FIG. 2. As mentioned above, the ultrasound imaging probe 20 is coupled by the cable 22 to one of the connectors 26, which are connected to an ultrasound signal path 40 of conventional design. As is well-known in the art, the ultrasound signal path 40 includes a transmitter (not shown) coupling electrical signals to the probe 20, an acquisition unit (not shown) that receives electrical signals from the probe 20 corresponding to ultrasound echoes, a signal processing unit (not shown) that processes the signals from the acquisition unit to perform a variety of functions such as isolating returns from specific depths or isolating returns from blood flowing through vessels, and a scan converter (not shown) that converts the signals from the signal processing unit so that they are suitable for use by the display 16. The processing unit in this example is capable of processing both B mode (structural) and Doppler signals for the production of various B mode and Doppler volumetric images, including spectral Doppler volumetric images. The ultrasound signal path 40 also includes a control module 44 that interfaces with a processing unit 50 to control the operation of the above-described units. The ultrasound signal path 40 may, of course, contain components in addition to those described above, and, in suitable instances, some of the components described above may be omitted.

The processing unit 50 contains a number of components, including a central processor unit ("CPU") 54, random access memory ("RAM") 56, and read only memory ("ROM") 58, to name a few. As is well-known in the art, the ROM 58 stores a program of instructions that are executed by the CPU 54, as well as initialization data for use by the CPU 54. The RAM 56 provides temporary storage of data and instructions for use by the CPU 54. The processing unit 50 interfaces with a mass storage device such as a disk drive 60 for permanent storage of data, such as data corresponding to ultrasound images obtained by the system 10. However, such image data is initially stored in an image storage device 64 that is coupled to a signal path 66 extending between the ultrasound signal path 40 and the processing unit 50. The disk drive 60 also preferably stores protocols which may be called up and initiated to guide the sonographer through various ultrasound exams.

The processing unit 50 also interfaces with the keyboard and controls 28. The keyboard and controls 28 may also be manipulated by the sonographer to cause the ultrasound system 10 to produce automatically generated reports at the conclusion of an examination. The processing unit 50 preferably interfaces with a report printer 80 that prints reports containing text and one or more images. The type of reports provided by the printer 80 depends on the type of ultrasound examination that was conducted by the execution of a specific protocol. Finally, as mentioned above, data corresponding to the image may be downloaded through a suitable data link, such as a network 74 or a modem 76, to a clinical information system 70 or other device.

Figure 3A:
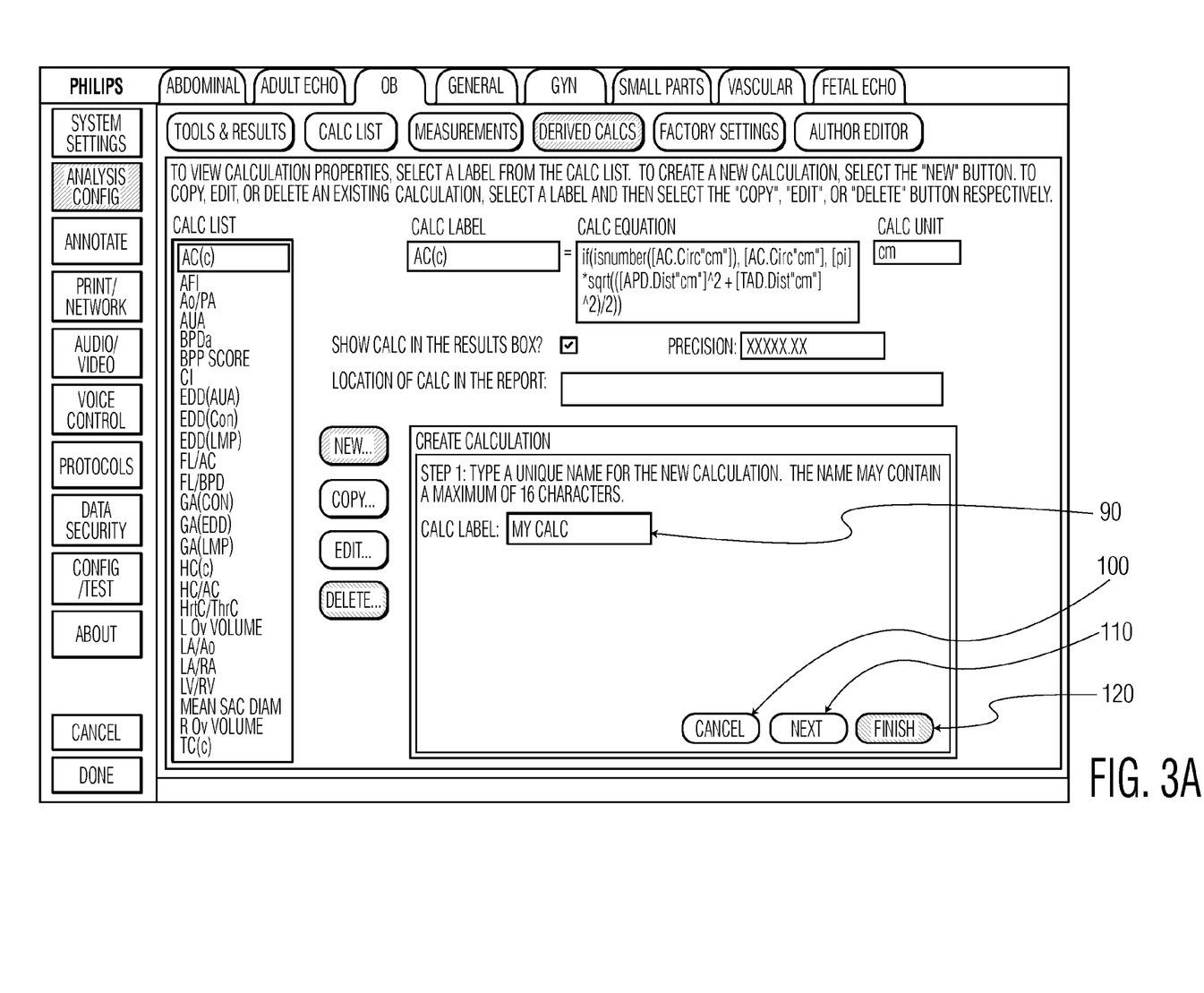
FIGS. 3a-3e illustrate a method for creating a custom calculation in one example of the present invention.
Figure 3B:
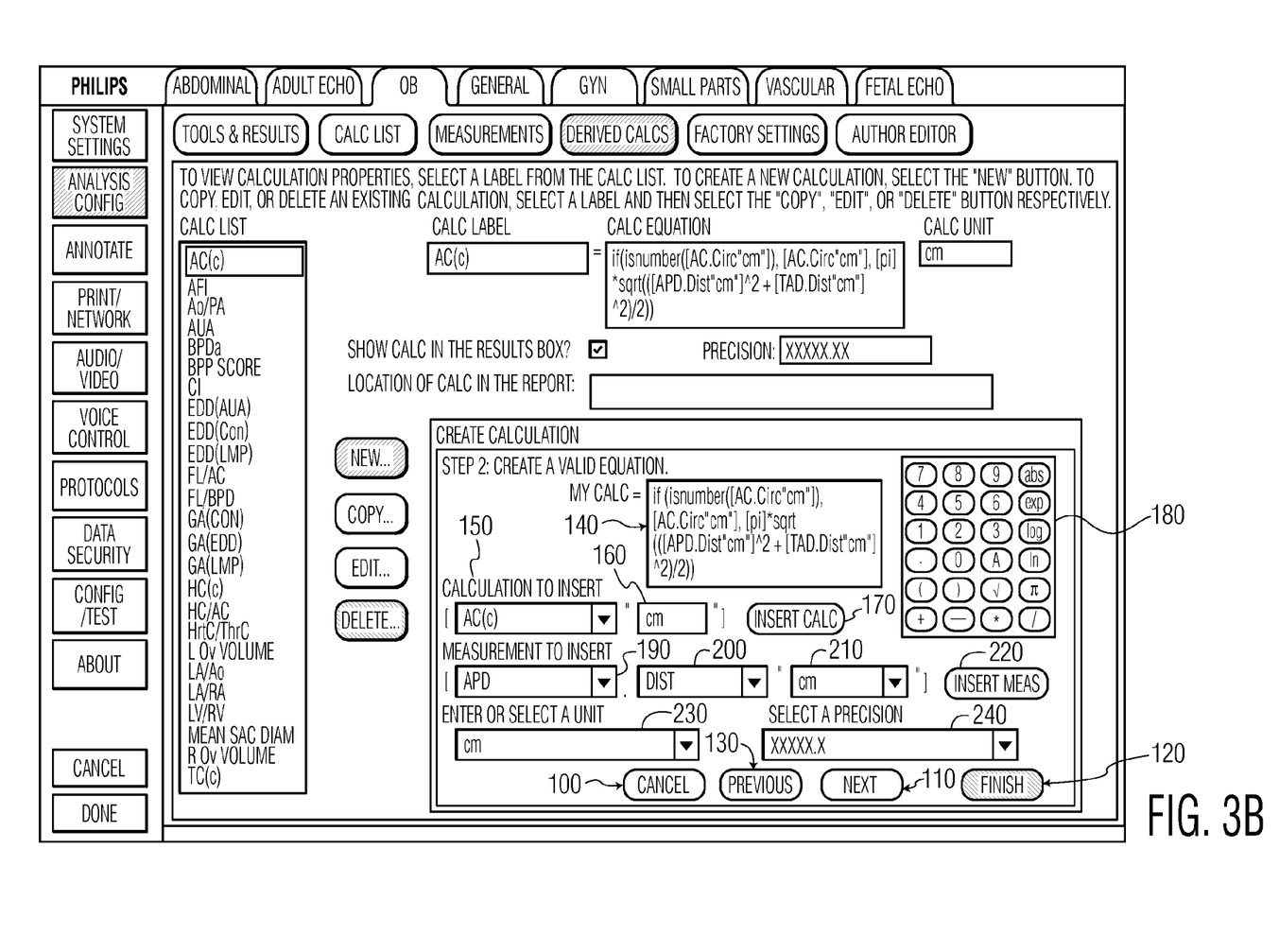

A procedure for creating a custom calculation according to one example of the present invention is illustrated in FIGS. 3a-3e. FIG. 3a illustrates an ultrasound image screen showing the first step in creating a custom calculation. In this example the sonographer may begin this procedure by tapping a predetermined softkey on the touchscreen display 18, as mentioned above. The sonographer must enter the Label in the Calc Label 90 field and then click on the Next 110 button. Also illustrated are the Cancel 100 button and the Finish 120 button. At this stage of the creation process, it is not possible to finish and save the equation since none has been entered nor verified as being valid. The Finish 120 button, therefore, is inactive. The Cancel 100 button functions to completely cancel the entire procedure. After the sonographer clicks on Next 110, but before the next screen is displayed, the system verifies that the Label is unique and that it is less than 16 characters. Once the information is verified, the next step, as illustrated in FIG. 3b, is displayed.

FIG. 3b illustrates an ultrasound image screen showing the second step in creating a custom calculation. In this step, the sonographer creates a valid custom equation in the Calc field 140. The sonographer may enter an equation directly into the Calc field 140 using the keyboard and/or onscreen touch Keypad 180. The equation may also contain the results of other calculations or measurements computed by or stored in the system. For example, the sonographer may symbolically insert a pre-defined or previously created custom calculation into the equation in the Calc field 140 by first selecting the calculation in the Calculation Dropdown 150, specifying the units of that calculation in the Calculation Units Dropdown 160 and clicking on the Insert Calc 170 button.

With further reference to FIG. 3b, the sonographer may likewise symbolically insert a previously stored measurement into the custom equation as shown in Calc field 140 by first, selecting the measurement in the Measurement Dropdown 190, selecting a parameter in the Measurement Parameter Dropdown 200, specifying the units of that measurement in the Measurement Units Dropdown 210 and clicking on the Insert Meas 220 button. The sonographer must select the units and precision of the new calculation by entering or selecting such in the Units Dropdown 230 and the Precision Dropdown 240 respectively. The sonographer then clicks the Next 110 button. After the sonographer clicks on Next 110, but before the next screen is displayed, the system verifies that the equation is valid. The Previous 130 button allows the sonographer to return to the previous screen and, in this example, change the Label for the calculation under construction. As discussed above, the Cancel 100 button functions to completely cancel the entire procedure. As with the previous step, it is not possible to finish and save the equation at this stage of the processes and the Finish 120 button, therefore, is inactive. After the equation is entered and verified, the next step, as illustrated in FIG. 3c, is displayed.

Figure 3C:
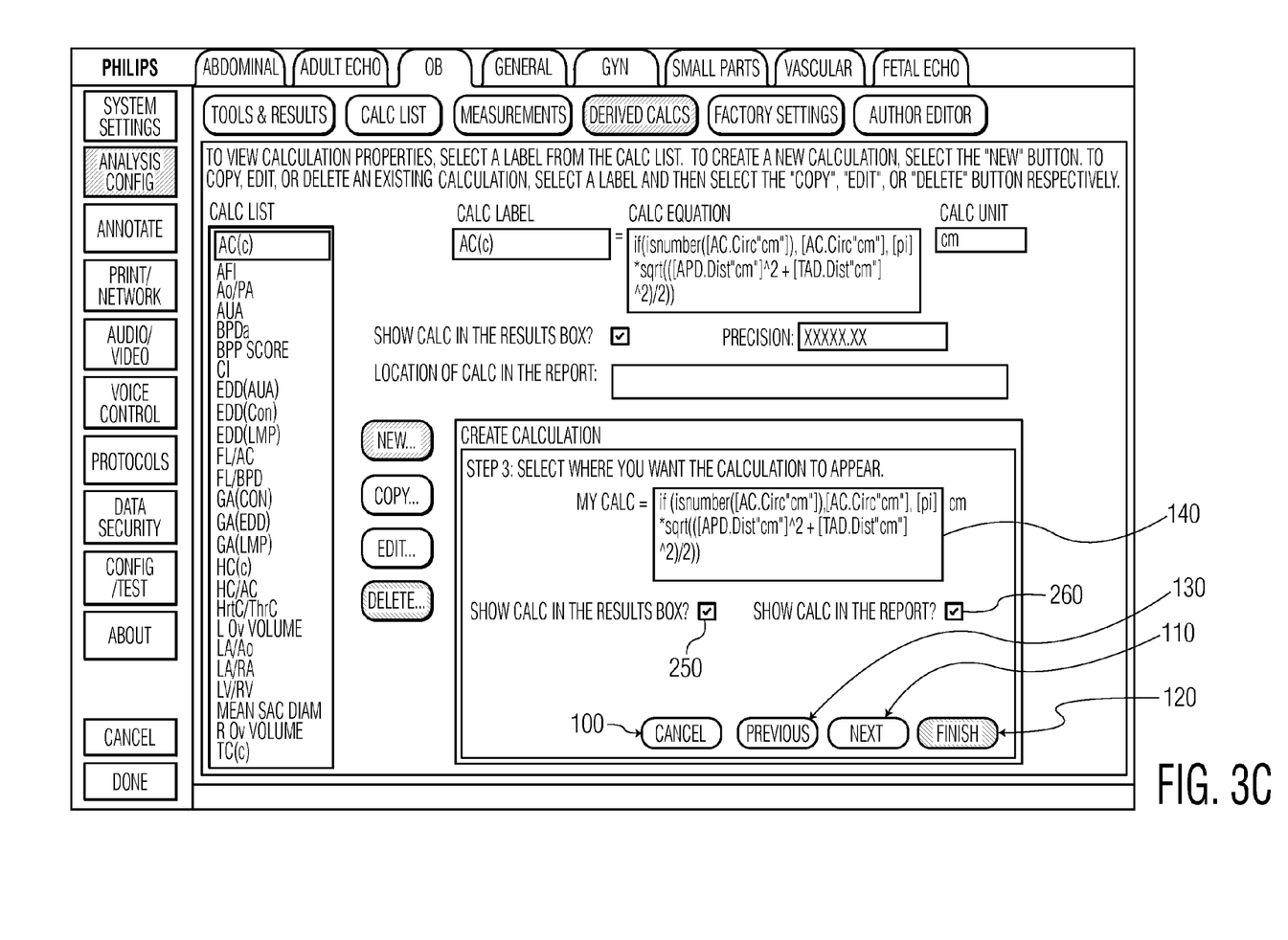

FIG. 3c illustrates an ultrasound image screen showing the third step in creating a custom calculation. In a this example of the present invention, the sonographer is able to specify where custom calculations will appear and be viewed during an exam or when generating reports. FIG. 3c illustrates one possible example of this capability. Custom calculations can be made to appear in either or both of a Results box or a final Report. The sonographer may have the calculation result appear in the Results box by checking the Results Checkbox 250. Likewise, if the sonographer would like the calculation to appear in the report, the Report Checkbox 260 should be selected. Until one or both of the checkboxes are selected, the Next 110 button is disabled because the calculation must be configured to be displayed in at least one of these two places. If only the Results Checkbox 250 is selected, the Finish 120 button will become active giving the sonographer the ability to complete the entire operation immediately. If the Report Checkbox 260 is selected, further information is required from the sonographer that is gathered in the next step. Because of this, the Finish 120 button is not active when the Report Checkbox 260 is selected. The Previous 130 button allows the sonographer to return to the previous screen to make changes and, as discussed above, the Cancel 100 button functions to completely cancel the entire procedure.

Figure 3D:
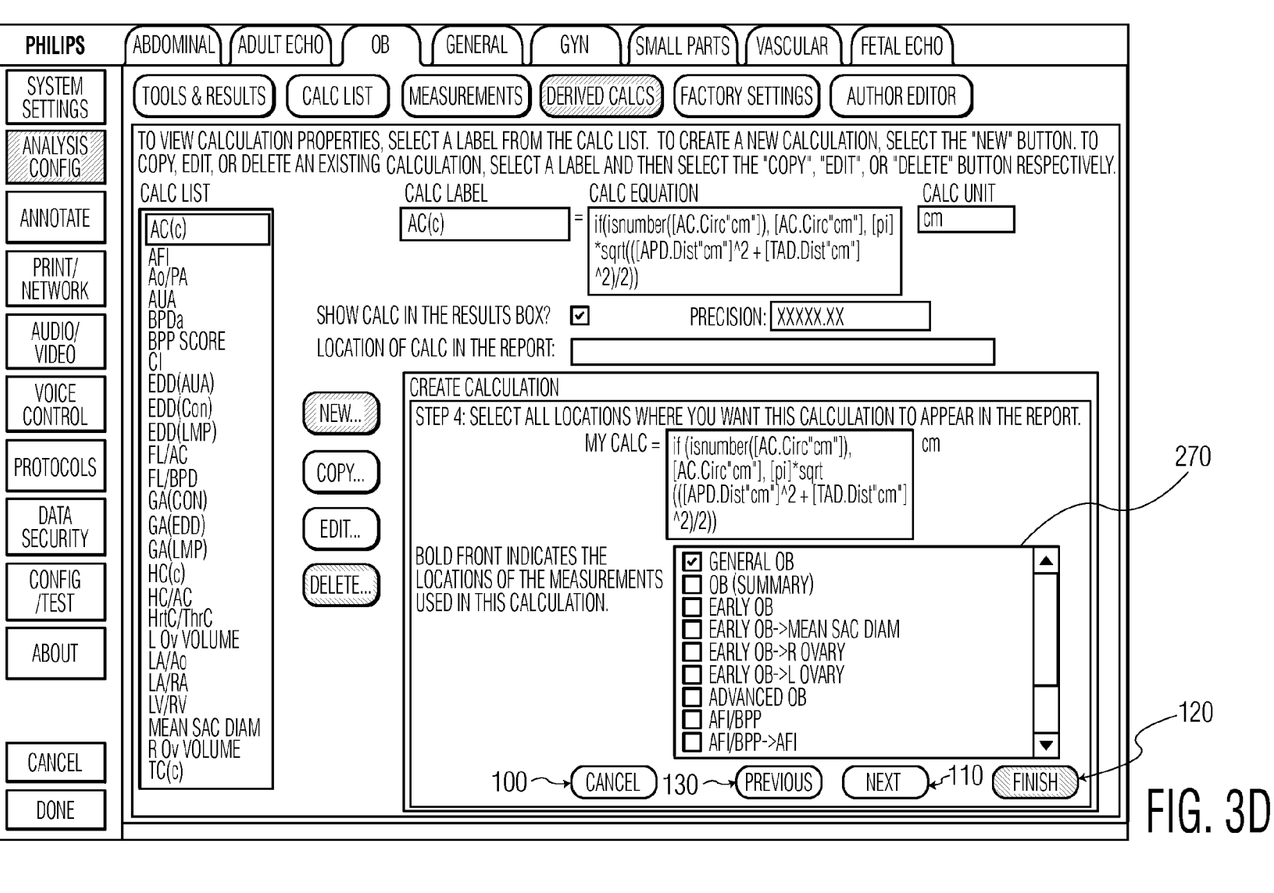

FIG. 3d illustrates an ultrasound image screen showing a fourth step in this example. This screen allows the sonographer to select the locations where the calculation is to appear within a report. The sonographer selects where the calculation is to appear by scrolling through the Location List 270 and selecting the checkbox for the appropriate location. More than one location may be selected, and the calculation will appear in every such location. The contents of the Location List 270 depends on what type of report is being generated, which in turn depends on what type of exam is being conducted. This screen is displayed for the sonographer only if the calculation was designated to be displayed in the previous step. As discussed above, the Cancel 100, Next 110 and Previous 130 buttons are all active and function to cancel the operation or move to the next or previous steps respectively. When the sonographer clicks either the Next 110 or Finish 120 buttons, the system verifies that at least one location in Location List 270 was selected. If the user has not selected at least one location, the user must either do so or click the Previous 130 button to return to the previous screen and deselect the Report Checkbox 260. The Finish 120 button allows the sonographer to complete the operation and store the newly created calculation. Clicking the Next 110 button instructs the system to display the next and final step in the procedure.

Figure 3E:
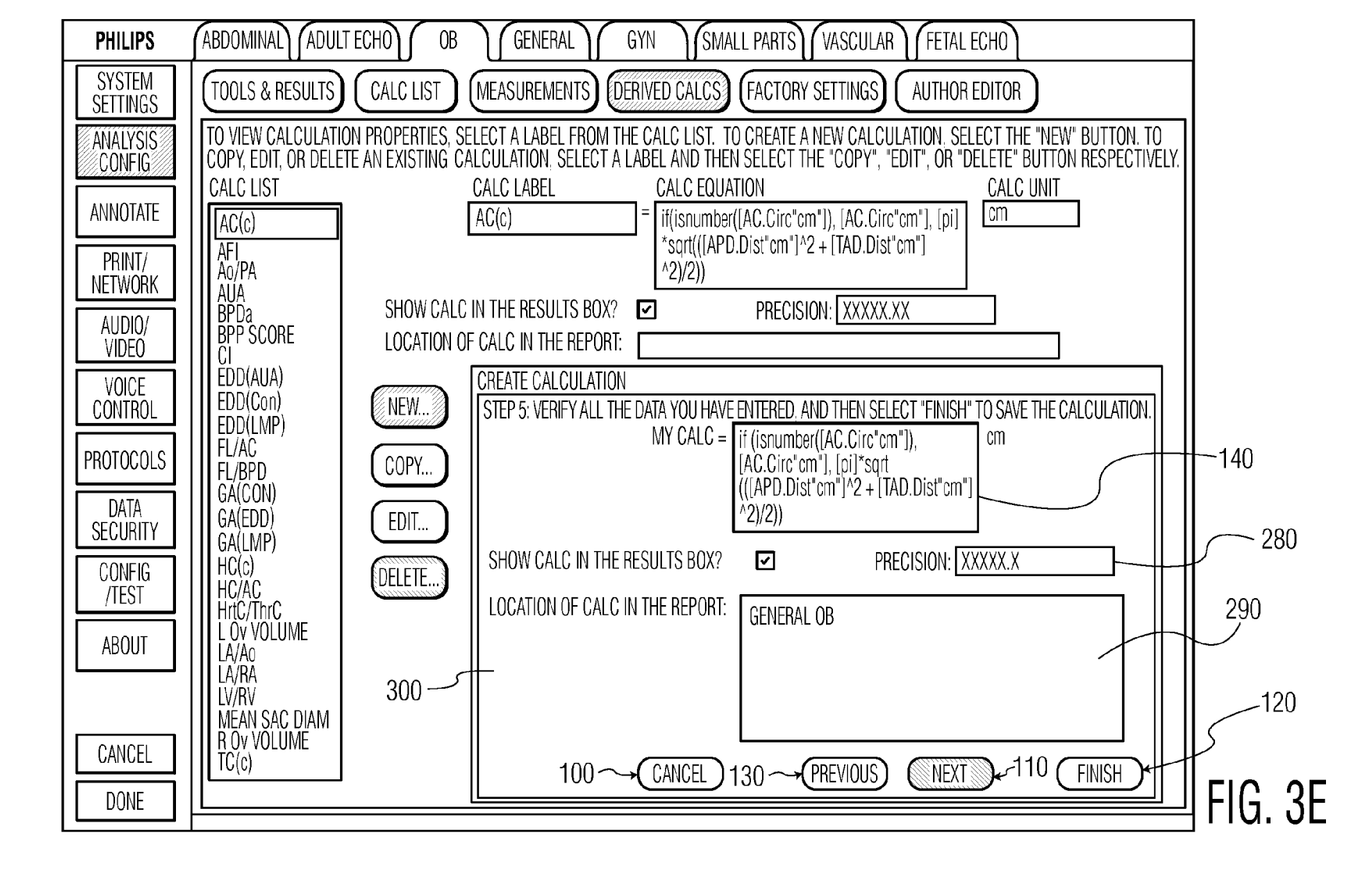

FIG. 3e illustrates an ultrasound image screen showing a fifth step in this example. This screen displays all the information the sonographer entered in previous steps and allows the sonographer to verify that the information is correct prior to saving the calculation. The Calc field 140 displays the custom equation. The Results Checkbox 300 shows whether or not the sonographer as designated the calculation to appear in the Results. The Precision 280 field displays the precision the sonographer selected for the results and finally, the Location Report 290 field lists all the locations in the report where the calculation will appear. At this stage of the procedure, all the data as entered has been verified as being syntactically valid. The sonographer may, however, find a mistake or wish to make revisions. To make such corrections, the sonographer must click the Previous 130 button one or more times to return to a previous step containing the information that is to be changed. As usual, the Cancel 100 button cancels the entire procedure. The Next 110 button is inactive during this step because this is the last step in the procedure. Finally, if the sonographer is satisfied with all the data, the Finish 120 button is clicked to save the calculation to the system.

Though this description of creating a custom calculation is made in terms of certain steps taking place in a certain order, it will be understood that the particular number of steps and their order is exemplary only. Other examples of the invention might contain more or fewer steps and may be presented to the sonographer in a different order. The Calc Label 90 as shown in FIG. 3a, for example, need not be specified in Step 1. Other steps in the creation procedure may proceed independently of the particular Calc Label the sonographer specifies. This step could, therefore, occur anywhere in the sequence.

The procedure for editing an existing calculation is quite similar to that of creating a new calculation. For example, the sonographer can select an existing calculation from a list displayed on the system screen and then click the Edit button to begin editing the calculation. The system then presents the sonographer with the appropriate series of screens, but with the existing calculation information pre-populated into the appropriate fields. The sonographer may then make changes to this information and save the changes.

The procedure for copying an existing calculation is shorter than that of editing or creating. When copying a calculation, the sonographer only need specify Calc Label 90 for the resulting copy as in FIG. 3a above. The copy is saved to the system after the label is entered and verified. The sonographer may then go through the steps explained above to make modifications to the copy as desired.

While the above examples illustrate the use of only ultrasound information, it should be understood that other patient information and information from other medical devices can be used in an equation. For example, patient data such as weight, age, and patient menstrual cycle may be entered and used in an equations, as may data from measurements by other devices such as of blood pressure or hematocrit.

What is claimed is:

1. In an ultrasound diagnostic system, a method for creating and managing ultrasound measurement-based equations, the method comprising:
   displaying on an ultrasound system display from a command sequence each of a plurality of steps necessary to create or manage at least one measurement-based equation;
   at each step, accepting information from the user necessary for creating or managing the measurement-based equation;
   verifying the accepted information; and
   saving the accepted and verified information of the measurement-based equation in the ultrasound system.

2. The method of claim 1 wherein accepting information from the user comprises accepting information from the user that adds at least one additional step to the command sequence.

3. The method of claim 1 wherein accepting information from the user comprises accepting information from the user that allows the user to skip at least one step in the command sequence.

4. The method of claim 1 wherein accepting information from the user comprises accepting information from the user that specifies the precision or units of the measurement-based equation.

5. The method of claim 1 wherein a command sequence is comprised of the steps necessary to create, edit, copy or delete a measurement-based equation.

* * * * *